United States Patent
Cosnek

(10) Patent No.: US 9,833,585 B2
(45) Date of Patent: Dec. 5, 2017

(54) HEART RATE COHERENCE USING RESPIRATORY THERAPY DEVICES

(71) Applicant: KONINKLIJKE PHILIPS N.V., Eindhoven (NL)

(72) Inventor: John Michael Cosnek, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 461 days.

(21) Appl. No.: 14/399,281

(22) PCT Filed: May 21, 2013

(86) PCT No.: PCT/IB2013/054182
§ 371 (c)(1),
(2) Date: Nov. 6, 2014

(87) PCT Pub. No.: WO2013/179181
PCT Pub. Date: Dec. 5, 2013

(65) Prior Publication Data
US 2015/0096564 A1    Apr. 9, 2015

Related U.S. Application Data

(60) Provisional application No. 61/654,167, filed on Jun. 1, 2012.

(51) Int. Cl.
*A61M 16/00*     (2006.01)
*A61B 5/0205*    (2006.01)
(Continued)

(52) U.S. Cl.
CPC ....... *A61M 16/0069* (2014.02); *A61B 5/0205* (2013.01); *A61M 16/0003* (2014.02);
(Continued)

(58) Field of Classification Search
CPC .......... A61M 16/0003; A61M 16/0051; A61M 16/0069; A61M 2016/0015;
(Continued)

(56) References Cited

U.S. PATENT DOCUMENTS 7,556,038 B2    7/2009   Kirby et al.
9,220,856 B2 *  12/2015  Martin .............. A61M 16/0051
(Continued)

FOREIGN PATENT DOCUMENTS

WO    2009138923 A1    11/2009
WO    2010133986 A1    11/2010

OTHER PUBLICATIONS

Johnson, "Why Do Monks Chant at 6 Breaths a Minute? Is It Beyond Science?", The 3rd World Conference on Buddhism and Science (WCBS), Undated, pp. 1-7.
(Continued)

*Primary Examiner* — Lynne Anderson

(57) ABSTRACT

Systems and methods for improving the heart rate coherence and/or heart rate variability of a subject use a respiratory therapy device to provide breathing cues that prompt a subject to breathe such that various respiratory and coronary parameters are aligned, for example in phase.

15 Claims, 3 Drawing Sheets

Figure 1:
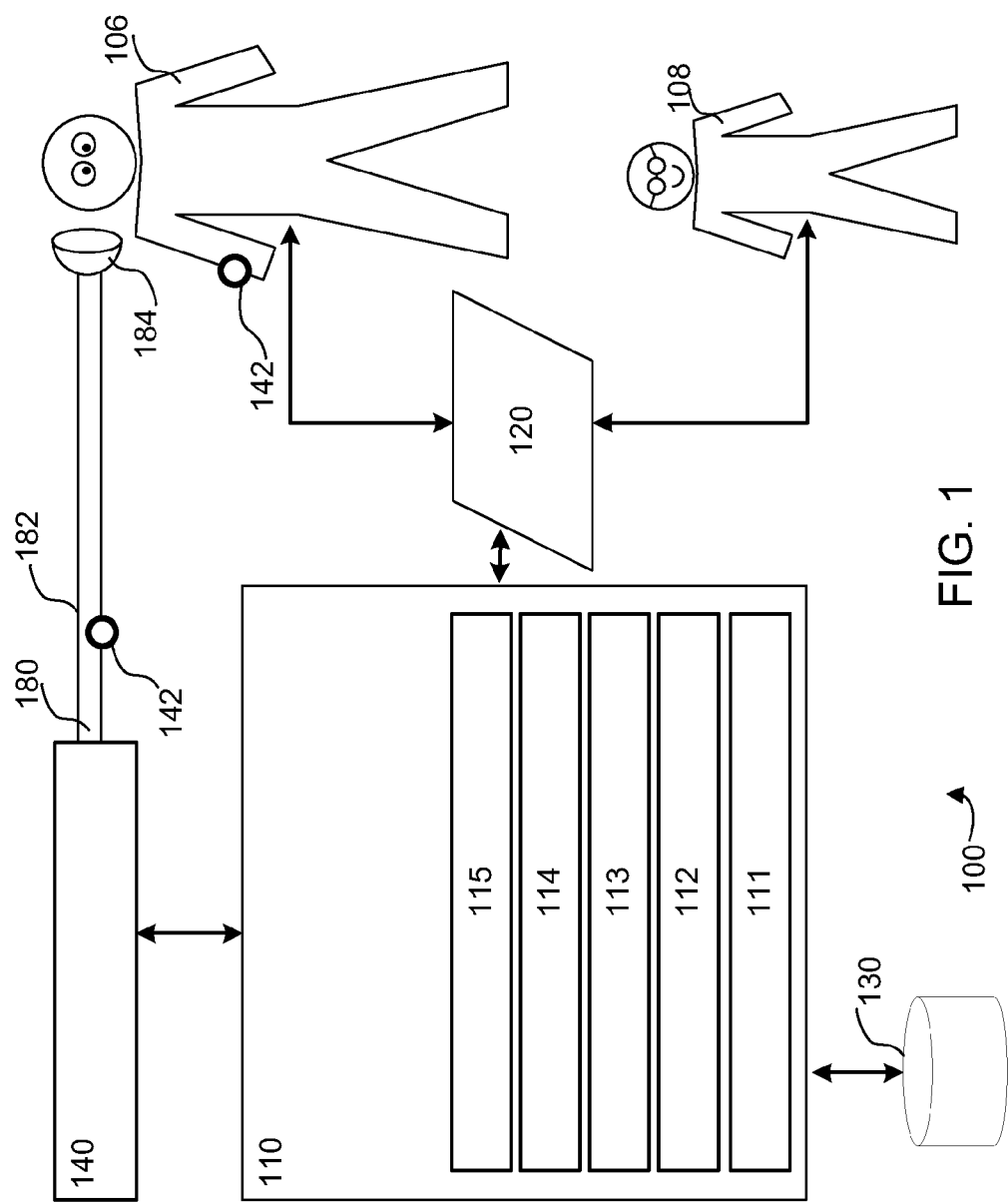

(51) Int. Cl.
  *A61M 16/16*  (2006.01)
  *A61M 16/06*  (2006.01)
  *A61M 16/08*  (2006.01)
  *A61M 16/10*  (2006.01)

(52) U.S. Cl.
  CPC ........ *A61M 16/0051* (2013.01); *A61M 16/06* (2013.01); *A61M 16/08* (2013.01); *A61M 16/161* (2014.02); *A61M 2016/0027* (2013.01); *A61M 2016/0033* (2013.01); *A61M 2016/102* (2013.01); *A61M 2205/18* (2013.01); *A61M 2205/3303* (2013.01); *A61M 2205/3317* (2013.01); *A61M 2205/3331* (2013.01); *A61M 2205/3365* (2013.01); *A61M 2205/3584* (2013.01); *A61M 2205/3592* (2013.01); *A61M 2205/50* (2013.01); *A61M 2205/505* (2013.01); *A61M 2205/52* (2013.01); *A61M 2230/04* (2013.01); *A61M 2230/06* (2013.01); *A61M 2230/10* (2013.01); *A61M 2230/205* (2013.01); *A61M 2230/30* (2013.01); *A61M 2230/42* (2013.01); *A61M 2230/60* (2013.01)

(58) Field of Classification Search
  CPC ...... A61M 2016/0027; A61M 2205/33; A61M 2205/3303; A61M 2205/3317; A61M 2205/3331; A61M 2205/3334; A61M 2205/3365; A61M 2205/3576; A61M 2205/3584; A61M 2205/3592; A61M 2205/50; A61M 2205/502; A61M 2205/505; A61M 2205/52; A61M 2230/005; A61M 2230/04; A61M 2230/06; A61M 2230/10; A61M 2230/205; A61M 2230/30; A61M 2230/42; A61M 2230/60; A61B 5/0205
  See application file for complete search history.

(56) References Cited

U.S. PATENT DOCUMENTS

| | | | |
|---|---|---|---|
| 9,597,468 B2* | 3/2017 | Schindhelm | ...... A61M 16/0051 |
| 2005/0096555 A1 | 5/2005 | Elliott | |
| 2005/0124906 A1 | 6/2005 | Childre et al. | |
| 2007/0173728 A1* | 7/2007 | Pu | ...................... A61B 5/02405 |
| | | | 600/484 |
| 2008/0035147 A1 | 2/2008 | Kirby et al. | |
| 2008/0066752 A1* | 3/2008 | Baker | ............... A61M 16/0051 |
| | | | 128/204.23 |
| 2011/0046434 A1 | 2/2011 | Schmeink et al. | |
| 2011/0213215 A1 | 9/2011 | Doyle et al. | |

OTHER PUBLICATIONS

Kristal-Boneh et al, "Heart Rate Variability in Health and Disease", Scandinavian Journal of Work Environment and Health, 1995, vol. 21, No. 2, pp. 85-95.
Fourie, "Effects of RSA Feedback on Post-Traumatic Stress Disorder Symptomatology", Bond University, Humanitites & Social Sciences Papers, 2006, pp. 1-9.
Yasuma et al, "Respiratory Sinus Arrhythmia Why Does the Heartbeat Synchronize With Respiratory Rhhythm?", Chest, vol. 125, No. 2, Feb. 2004, pp. 683-.
Cysarz et al, "Cardiorespiratory Synchronization During Zen Meditation", European Journal of Applied Physiology, vol. 95, Issue 1, 2005, p. 88.
Giardino et al, "Respiratory Sinus Arrhythmia is Associated With Efficiency of Pulmonary Gas Exchange in Healthy Humans", American Journal of Physiology Heart Circulatory Physiology, vol. 284, 2003, pp. H1585-H1591.
Heart Tracker, Stress Managmenet Tool for Home Use, http://www.biof.com/hearttracker.asp, Downloaded Nov. 3, 2014.
Emwave Pro for MAC and PC, http://store.heartmath.org/emwave-pc/emwave-desktop-mac-pc, Downloaded, 2 Pages. Nov. 3, 2014.
Stresseraser, Owner's Manual, Copyright 2007, Helicor Inc. 64 Pages.

* cited by examiner

HEART RATE COHERENCE USING RESPIRATORY THERAPY DEVICES

CROSS-REFERENCE TO PRIOR APPLICATIONS

This application is the U.S. National Phase application under 35 U.S.C. §371 of International Application No. PCT/IB2013/054182, filed on May 21, 2013 which claims the benefit of U.S. Provisional Patent Application No. 61/654,167, filed on Jun. 1, 2012. These applications are hereby incorporated by reference herein.

The present disclosure pertains to systems and methods for improving heart rate variability and/or heart rate coherence of subjects using a respiratory therapy device, and, in particular, providing breathing cues to prompt and/or guide a subject such that the breathing pattern is aligned with the heart rate pattern of the subject.

It is known that some types of respiratory therapy involve the delivery of a flow of breathable gas to the airway of a subject. It is known that a flow of breathable gas may be pressurized at varying levels of pressure, even during a single therapy session and/or a single respiratory cycle. It is known that respiratory therapy may be delivered through and/or provided by respiratory therapy device such as, e.g., (multi-level) positive airway pressure devices. It is known that certain health benefits may be related to the respiratory pattern of a subject.

It is known that the pattern of a subject's heartbeat may change gradually over the course of multiple respiratory cycles. It is known that a subject's heart rate, even at rest or in a calm state, may increase at the onset of an inhalation and/or decrease at the onset of an exhalation.

Accordingly, it is an object of one or more embodiments of the present invention to provide a system for improving heart rate coherence of a subject. The system includes a pressure generator, sensors, one or more processors, and processing modules. The pressure generator is configured to generate a pressurized flow of breathable gas for delivery to the airway of the subject. The sensors are configured to generate output signals conveying information related to i) one or more gas parameters of the pressurized flow of breathable gas and ii) a heart rate of the subject. The one or more processors are configured to execute processing modules. The processing modules include a control module, a respiratory parameter determination module, a coronary parameter determination module, and a target module. The control module is configured to adjust levels of one or more gas parameters of the pressurized flow of breathable gas to provide breathing cues to the subject that prompt to transition between breathing phases. The respiratory parameter determination module is configured to determine a breathing rate and breathing phases of the subject based on the generated output signals. The coronary parameter determination module is configured to determine a heart rate variability for the subject, wherein the heart rate variability is based on the heart rate of the subject. The target module is configured to determine a target breathing rate range and target breathing phases for which the heart rate variability is phase-aligned with the breathing rate and breathing phases of the subject. The control module adjusts the levels of one or more gas parameters of the pressurized flow of breathable gas to guide the subject to breathe according to the determined target breathing phases and within the determined target breathing rate range.

It is yet another aspect of one or more embodiments of the present invention to provide a method for improving heart rate coherence implemented in a system including a pressure generator and sensors. The method comprises generating a pressurized flow of breathable gas for delivery to the airway of the subject; generating output signals conveying information related to one or more gas parameters of the pressurized flow of breathable gas, and a heart rate of the subject; adjusting levels of one or more gas parameters of the pressurized flow of breathable gas to provide breathing cues to the subject that prompt the subject to transition between breathing phases; determining a breathing rate and breathing phases of the subject based on the generated output signals; determining a heart rate variability for the subject, wherein the heart rate variability is based on the heart rate of the subject; and determining a target breathing rate range and target breathing phases for which the heart rate variability is phase-aligned with the breathing rate and breathing phases of the subject, wherein adjustments of the levels of one or more gas parameters of the pressurized flow of breathable gas guide the subject to breathe according to the determined target breathing phases and within the determined target breathing rate range.

It is yet another aspect of one or more embodiments to provide a system for improving heart rate coherence. The system includes means for generating a pressurized flow of breathable gas for delivery to the airway of the subject; means for generating output signals conveying information related to one or more gas parameters of the pressurized flow of breathable gas, and a heart rate of the subject; means for adjusting levels of one or more gas parameters of the pressurized flow of breathable gas to provide breathing cues to the subject that prompt the subject to transition between breathing phases; means for determining a breathing rate and breathing phases of the subject based on the generated output signals; means for determining a heart rate variability for the subject, wherein the heart rate variability is based on the heart rate of the subject; and means for determining a target breathing rate range and target breathing phases for which the heart rate variability is phase-aligned with the breathing rate and breathing phases of the subject, wherein the means for adjusting levels of one or more gas parameters guides the subject to breathe according to the determined target breathing phases and within the determined target breathing rate range.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 2A:
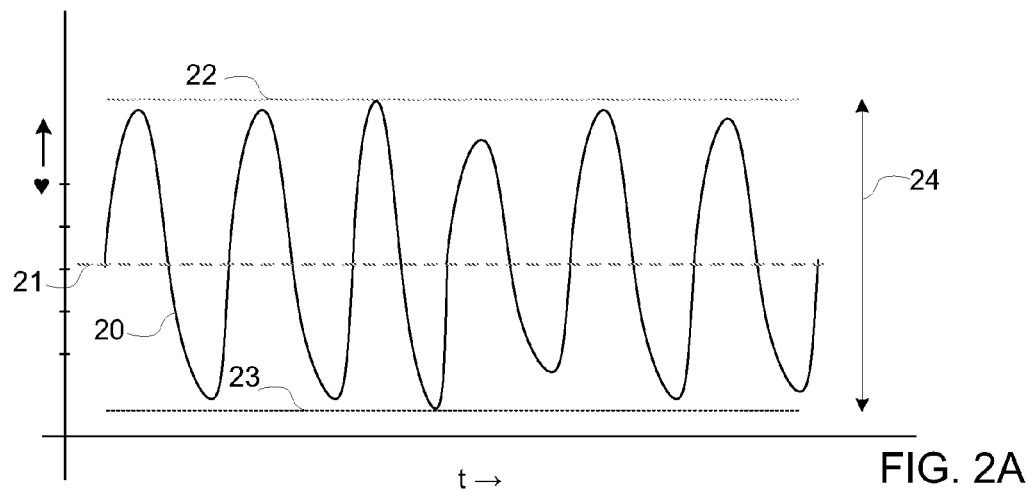
Figure 2B:
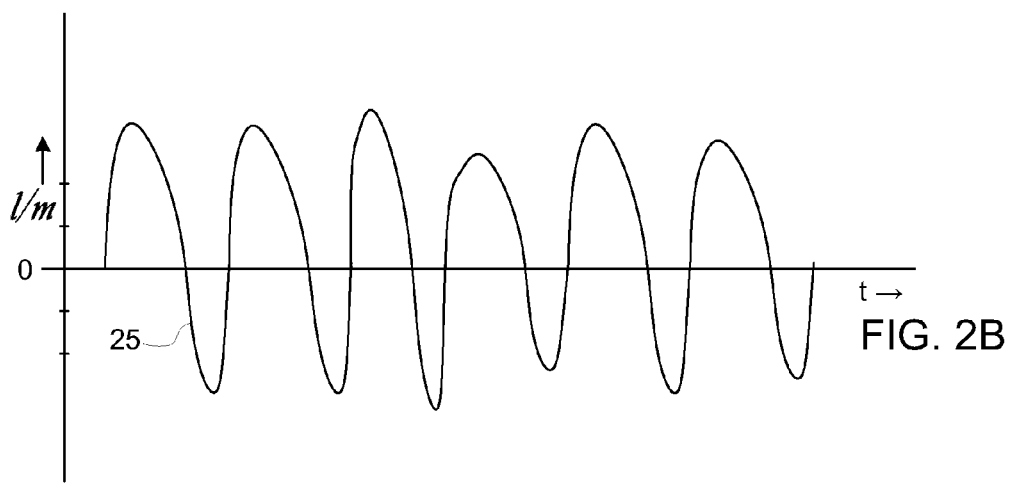
Figure 2C:
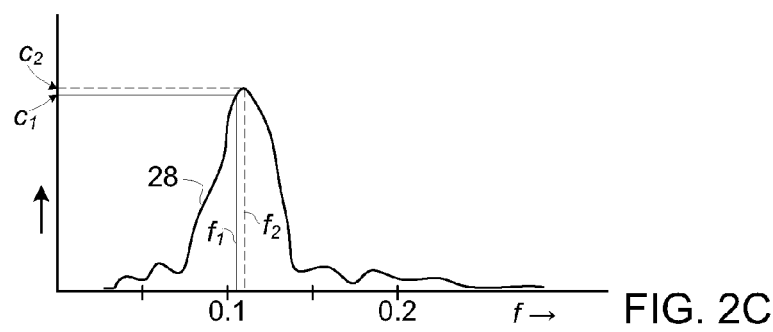
Figure 3:
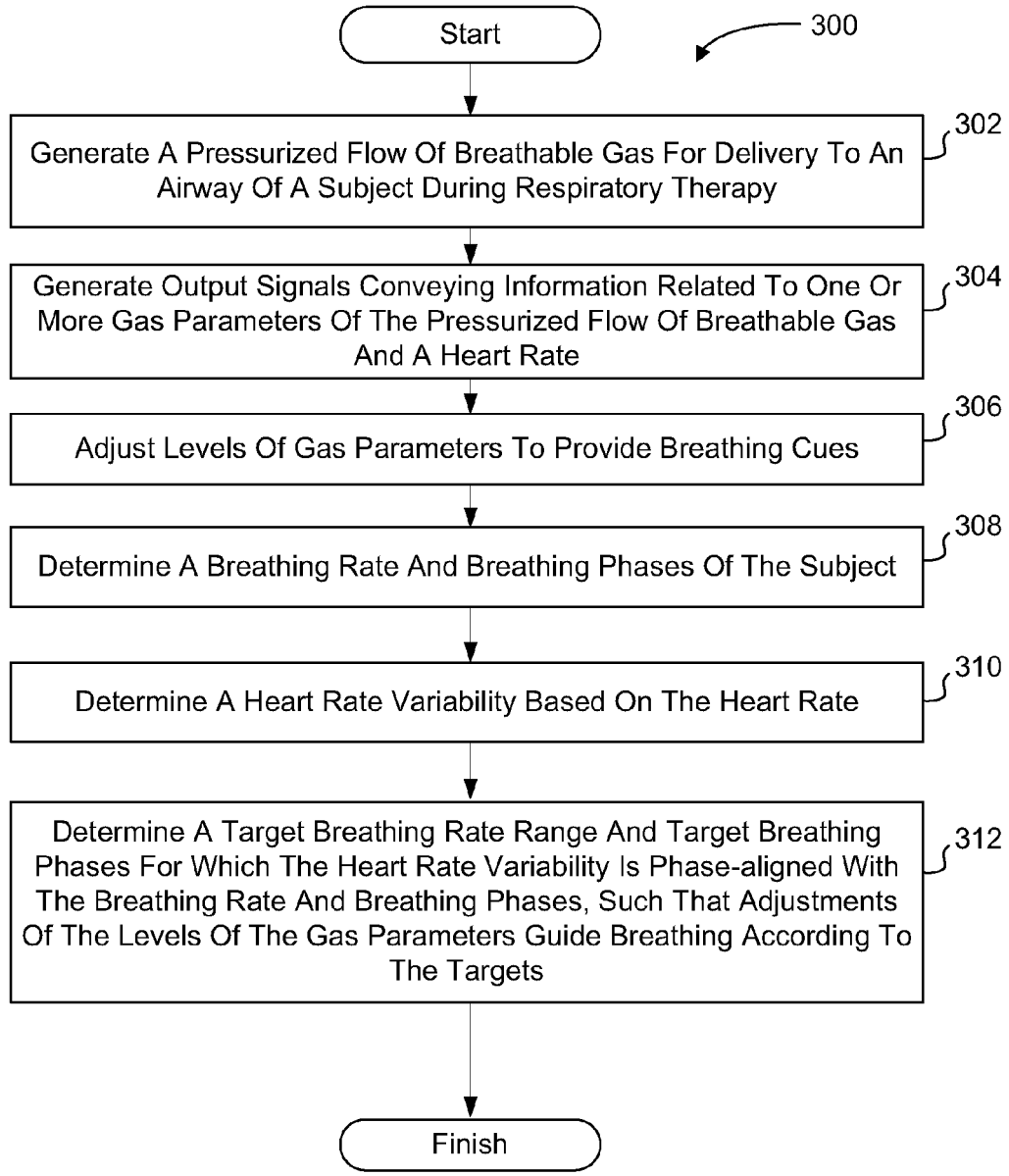

FIG. 1 schematically illustrates a system for improving heart rate coherence and/or heart rate variability of a subject according to one or more embodiments;

FIGS. 2A-2B-2C illustrate exemplary graphs of heart rate, respiratory flow rate and a frequency distribution of the heart rate signal; and FIG. 3 illustrates a method for improving heart rate coherence and/or heart rate variability of a subject according to one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 100 for improving heart rate coherence and/or heart rate variability of a subject 106. System 100 may be implemented as, integrated with, and/or operating in conjunction with a respiratory therapy device. In some embodiments, one or more operative levels (e.g. pressure, volume, etc.) are adjusted on a relatively ongoing manner (e.g., each breath, every few breaths, every few seconds, etc.) during an individual therapy session to titrate the therapy. Alternatively, and/or simultaneously, adjustments may be made more intermittently and/or between therapy sessions as well as during therapy sessions. Heart rate variability may be defined as the difference between a maximum heart rate and a minimum heart rate in a particular period of time. Heart rate coherence may quantify how well variations in heart rate are aligned with and/or match variations in respiration, as described in more detail elsewhere herein.

System 100 includes one or more of a pressure generator 140, a delivery circuit 180, sensors 142, an electronic storage 130, a user interface 120, a processor 110, a control module 111, a respiratory parameter determination module 112, a coronary parameter determination module 113, a target module 114, a domain conversion module 115, and/or other components.

Pressure generator 140 of system 100 in FIG. 1 may be integrated, combined, or connected with a ventilator and/or (positive) airway pressure device (PAP/CPAP/BiPAP®/etc.) and configured to provide a pressurized flow of breathable gas for delivery to the airway of subject 106, e.g. via delivery circuit 180. Delivery circuit 180 may sometimes be referred to as subject interface 180. Subject 106 may or may not initiate one or more phases of respiration. Respiratory therapy may be implemented as pressure control, pressure support, volume control, and/or other types of support and/or control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Adjustments may be made numerous times in implementations using auto-titrating for providing respiratory support through the delivery of the pressurized flow of breathable gas. Pressure generator 140 is configured to adjust one or more of pressure levels, flow, humidity, velocity, acceleration, and/or other parameters of the pressurized flow of breathable gas, e.g. in substantial synchronization with the breathing cycle of the subject.

A pressurized flow of breathable gas is delivered from pressure generator 140 to the airway of subject 106 via a delivery circuit 180. Delivery circuit 180 may include a conduit 182 and/or a subject interface appliance 184. Conduit 182 may include a flexible length of hose, or other conduit, either in single-limb or dual-limb configuration that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 of system 100 in FIG. 1 is configured to deliver the pressurized flow of breathable gas to the airway of subject 106. As such, subject interface appliance 184 may include any appliance suitable for this function. In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

Electronic storage 130 of system 100 in FIG. 1 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, SD Card, etc.), and/or other electronically readable storage media (e.g. included on a Smart Card). Electronic storage 130 may store software algorithms, information determined by processor 110, information received via user interface 120, and/or other information that enables system 100 to function properly. For example, electronic storage 130 may record or store one or more gas and/or respiratory parameters (as discussed elsewhere herein), and/or other information. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to user 108 is a report detailing information recorded during one or more therapy sessions. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize system 100. Other exemplary input devices and techniques adapted for use with system 100 as user interface 120 include, but are not limited to, an RS-232 port, a Bluetooth link, an RF link, an IR link, modem (telephone, cable, Ethernet, Wi-Fi, WiMax, internet or other). In short, any technique for communicating information to and/or from system 100 is contemplated as user interface 120.

Sensors 142 of system 100 in FIG. 1 are configured to generate output signals conveying information and/or measurements related to parameters of respiratory airflow and/or airway mechanics, as well as the heart rate of subject 106. These parameters may include one or more of flow, (airway) pressure, humidity, velocity, acceleration, parameters associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject, and/or other parameters. One or more of the sensors 142 may be in fluid communication with conduit 182 and/or subject interface appliance 184. One or more of the sensors 142 may generate output signals related to physiological parameters pertaining to subject 106. For example, one or more of the sensors 142 may include a flow sensor, a flow meter, a gas meter, a thermometer, a current sensor, an electro-optical sensor, an infra-red sensor, a proximity-sensor, a hygrometer, a pressure sensor, an oxygen sensor, an oximetry sensor, a pulse oximeter, a blood pressure sensor, electroencephalography (EEG) sensors, magnetoencephalography (MEG) sensors, electrocardiography (EKG) sensors, (cardiac) ultrasound sensors, and/or other sensors.

The illustration of sensors 142 including two members in FIG. 1 is not intended to be limiting. The illustration of a sensor at or near subject interface appliance 184 is not intended to be limiting. For example, one or more sensors may be integrated and/or embedded with pressure generator 140. A parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement that may serve as a proxy for any of the previously listed parameters through a previously known and/or calibrated mathematical relationship. Resulting signals or information from sensors 142 may be transmitted to processor 110, user interface 120, electronic storage 130, and/or other components of system 100. This transmission may be wired and/or wireless.

Processor 110 of system 100 in FIG. 1 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of control module 111, respiratory event module 112, therapy module 113, usage module 114, starting level module 115, parameter determination module 116, timing module 117, and/or other modules. Processor 110 may be configured to execute modules 111-115 by software; hardware; firmware; some combination of software, hardware, and/or firmware; and/or other mechanisms for configuring processing capabilities on processor 110.

It should be appreciated that although modules 111-115 are illustrated in FIG. 1 as being co-located within a single processing unit, in embodiments in which processor 110 includes multiple processing units, one or more of modules 111-115 may be located remotely from the other modules. The description of the functionality provided by the different modules 111-115 described herein is for illustrative purposes, and is not intended to be limiting, as any of modules 111-115 may provide more or less functionality than is described. For example, one or more of modules 111-115 may be eliminated, and some or all of its functionality may be incorporated, shared, integrated into, and/or otherwise provided by other ones of modules 111-115. Note that processor 110 may be configured to execute one or more additional modules that may perform some or all of the functionality attributed below to one of modules 111-115.

Control module 111 is configured to control operation of system 100 during respiratory therapy sessions. Control module 111 may be configured to control the pressure generator to adjust one or more levels of one or more gas parameters of the pressurized flow of breathable gas to provide breathing cues to subject 106 that prompt subject 106 to transition between breathing phases. Gas parameters of the pressurized flow of breathable gas may be varied over time in accordance with a respiratory therapy regimen. Control module 111 may be configured to control pressure generator 140 to provide the pressurized flow of breathable gas at inhalation pressure levels during inhalation phases, and/or at exhalation pressure levels during exhalation phases. Information and/or parameters determined by other modules and/or received through sensors 142 may be used by control module 111, e.g. in a feedback manner, to adjust one or more therapy modes/settings/operations of system 100. Alternatively, and/or simultaneously, signals and/or information received through user interface 120 may be used by control module 111, e.g. in a feedback manner, to adjust one or more therapy modes/settings/operations of system 100. Control module 111 may be configured to time its operations relative to the transitional moments in the breathing cycle of a subject, over multiple breath cycles, and/or in any other relation to the timing of particular moments and/or (respiratory) events. One or more levels of one or more gas parameters may be adjusted such that other parameters, for example respiratory parameters, coronary parameter, and/or other physiological parameters are increased or decreased as desired.

Respiratory parameter determination module 112 of system 100 in FIG. 1 is configured to determine one or more gas parameters, respiratory parameters, and/or other physiological parameters from output signals generated by sensor(s) 142. The one or more gas parameters may include and/or be related to one or more of (peak) flow, flow rate, (tidal) volume, pressure, temperature, humidity, velocity, acceleration, gas composition (e.g. concentration(s) of one or more constituents such as, e.g., $H_2O$ and/or $CO_2$), thermal energy dissipated, volume of (intentional) gas leaked, and/or other measurements related to the (pressurized) flow of breathable gas and/or derivatives of such measurements. One or more respiratory parameters may be derived from gas parameters and/or other output signals conveying information and/or measurements of the pressurized flow of breathable gas. The one or more respiratory parameters may include one or more of respiratory rate, respiratory period, breathing phases, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other respiratory parameters and/or derivatives thereof.

By way of illustration, FIG. 2B illustrates an exemplary graph 25 of respiratory flow rate (in liters per minute) as the flow rate changes over time. Individual sinusoidal shapes in FIG. 2B may correspond to individual respiratory cycles of a patient. The X-axis depicts a flow rate of zero liters per minute. Inhalations are depicted by positive flow rates. Exhalations are depicted by negative flow rates. FIG. 2B illustrates approximately six respiratory cycles in an exemplary time period of about 1 minute. Note that the values in this example are not intended to be limiting in any way. Certain health benefits may be related to breathing slowly, for example at a rate between about five breaths per minute and about ten breaths per minute. Referring to FIG. 1, the breathing cues provided through control module 111 and pressure generator 140 may guide the breathing pattern (e.g. breathing rate and breathing phases) of subject 106 and/or prompt transitions between breathing phases of subject 106 such that subject 106 achieves a target breathing rate or target breathing rate range, for example between about five breaths per minute and about ten breaths per minute.

Coronary parameter determination module 113 of system 100 in FIG. 1 is configured to determine one or more coronary parameters, vascular parameters, and/or other physiological parameters from output signals generated by sensor(s) 142. The one or more physiological parameters may include and/or be related to one or more of heart rate, heart period, heart phase, heart rate curve shape, maximum or peak heart rate, minimum heart rate, peak-to-peak period, maximum rate increase, maximum rate decrease, average heart rate, other parameters related to heart rate and/or derivatives thereof, blood pressure, oxygen saturation, brain activity, heart function, and/or other parameters and combinations/ratios of multiple parameters. One or more coronary parameters may be derived from output signals generated by one or more sensors of sensors 142 depicted in FIG. 1. Coronary parameter determination module 113 may be configured to determine a heart rate variability for subject 106, for example based on the heart rate of subject 106. Coronary parameter determination module 112 and/or respiratory parameter determination module 112, individually and/or jointly, may be configured to determine heart rate coherence for subject 106. Heart rate coherence may quantify how well variations in heart rate are aligned with and/or match variations in respiration, as described in more detail in relation to domain conversion module 115, below.

By way of illustration, FIG. 2A illustrates an exemplary graph 20 of a heart rate as it changes over time. The time period depicted in FIG. 2A along the X-axis may be about 1 minute. The heart rate depicted in FIG. 2A appears to fluctuate and/or vary around a rate indicated by indicator 21. For example, the indicated rate may be about 60 beats per minute (BPM). Note that this may be patient-specific and session-specific, and the actual values depicted in the examples of FIG. 2A are not intended to be limiting in any way. As depicted in FIG. 2A, a heart rate variability 24 may be defined as the difference between a maximum heart rate 22 and a minimum heart rate 23 for a particular period of time. Various types of statistical manipulation are considered, such as mean, median, and/or average heart rate. Heart rate variability 24 may be determined after a fixed period of time has passed, as a sliding window of a fixed and/or variable length, after every respiratory cycle, and/or continuously at predetermined time increments. For example, heart rate variability 24 may be determined about every 0.1 seconds, about every second, about every 10 seconds, about every 30 seconds, about every minute, and/or at other fixed and/or variable intervals. As an example in FIG. 2A, maximum heart rate 22 may be about 64 BPM, and minimum heart rate 23 may be about 56.5 BPM. Higher heart rate variability, particularly during slow or regular breathing, is generally considered beneficial for patients and/or indicative of healthy physiological conditions. Note that the X-axis indicating time may use the same or similar scale on FIG. 2A and FIG. 2B.

Referring to FIG. 1, target module 114 is configured to determine a target breathing rate and/or a target breathing rate range for subject 106. In some embodiments, determinations by target module 114 may be intended to affect one or more physiological parameters of subject 106, including, for example, heart rate, heart rate variability, and/or heart rate coherence. In some embodiments, determinations by target module 114 may be intended such that the breathing rate matches and/or aligns with the heart rate. Alternatively, and/or simultaneously, determinations by target module 114 may be intended such that the breathing phases match and/or align with the phases of the heart rate. Phase-alignment may be defined as a condition wherein the measured phase of multiple variables (e.g. parameters and/or sensor readings) are within a predetermined period of time or angle of each other. For example, the predetermined period of time may be about 0.1 seconds, about 0.5 seconds, about 1 second, about 2 seconds, about 3 seconds, about 4 seconds, about 5 seconds, and/or another suitable period of time. For example, phase-alignment between the heart rate variability and the breathing phases may be defined as a condition wherein peaks in the heart rate are determined to occur within a predetermined period of time from peaks of inspiratory flow rate. Alternatively, and/or simultaneously, phase alignment may be defined as a condition wherein nadirs in the heart rate are determined to occur within a predetermined period of time from peaks of expiratory flow rate. Control module 111 may adjust the levels of one or more gas parameters of the pressurized flow of breathable gas to guide subject 106 to breathe according to one or more determinations and/or targets as determined by target module 114.

In some embodiments, target module 114 may be configured to determine whether modifications of, e.g., the target breathing rate correspond to a change in one or more physiological parameters. For example, target module 114 may titrate the target breathing rate within a particular range of breathing rates in search of an increased heart rate variability. For example, a target breathing rate range may be between about 5.5 breaths per minute and about 7.5 breaths per minute. Through titration (and/or other ways implement a similar search), target module 114 may determine which target breathing rate in this range corresponds to an increased heart rate variability and/or the highest heart rate variability within this range. Once such a determination has been made, target module 114 may use that determined target breathing rate (which may be patient-specific) to improve the heart rate variability of subject 106 during respiratory therapy. As a specific patient's condition and/or medical state change over time, for example as a result of multiple therapy sessions, the target breathing rate that corresponds to the highest heart rate variability may change. It is envisioned that target module 114 may perform titration in order to find a particular target breathing rate repeatedly, for example at intervals of one week, two weeks, one month, an/or other appropriate intervals. Note that titration may similarly be used for other physiological parameters.

In some embodiments, target module 114 may be configured to determine whether modifications of, e.g., the target breathing rate correspond to a change in one or more physiological parameters, including for example blood pressure, oxygen saturation, brain activity, heart function, and/or other physiological parameters. Target module 114 may titrate the target breathing rate, e.g. within a particular target breathing rate range, to find a reduced and/or lowest blood pressure, an increased and/or highest oxygen saturation, an increase or decrease of a particular type of brain activity, an increase or decrease of a particular heart function, etc. Heart functions may pertain to one or more of the P wave, the PR interval, the PR segment, the QRS complex, the ST segment, the T wave, the ST interval, the QT interval, the U wave, the J wave, and/or other functions/periods/amplitudes that may be measured using EKG, derivatives thereof, and/or combinations thereof. Additionally, heart functions may pertain to levels, functions, periods, and/or amplitudes that may be measured by techniques other than EKG. Physiological parameters may thus be affected through use of a particular target breathing rate and/or particular target breathing phases.

Domain conversion module 115 is configured to convert and/or determine parameters from the time domain into a frequency domain, e.g. through a Fourier transformation. For example, domain conversion module 115 may be configured to convert and/or determine the breathing rate from the time domain to a breathing frequency distribution in a frequency domain. The breathing frequency distribution may be referred to as a breathing spectrum. The breathing frequency distribution may be depicted as a graph illustrating magnitude of energy amplitude for a range of frequencies.

Domain conversion module 115 may be configured to convert and/or determine the heart rate from the time domain to a heart frequency distribution in a frequency domain. The heart frequency distribution may be referred to as a heartbeat spectrum. The heart frequency distribution may be depicted as a graph illustrating magnitude of energy amplitude for a range of frequencies.

Conversions by domain conversion module 115 may be performed after a fixed period of time has passed, as a sliding window of a fixed and/or variable length, after every respiratory cycle, and/or continuously at predetermined time increments. For example, conversions may be performed about every 0.1 seconds, about every second, about every 10 seconds, about every 30 seconds, about every minute, and/or at other fixed and/or variable intervals.

Responsive to determination of the breathing frequency distribution, domain conversion module 115 and/or respiratory parameter determination module 112 may be configured to determine a fundamental frequency of the breathing frequency distribution and/or the frequency having the highest magnitude of energy amplitude in the breathing frequency distribution.

Domain conversion module 115 and/or coronary parameter determination module 113 may be configured to determine heart rate coherence of subject 106. Heart rate coherence may be based on the magnitude of energy amplitude of the heart frequency distribution at a particular frequency. The particular frequency may be the fundamental frequency of the breathing frequency distribution and/or the frequency having the highest magnitude of energy amplitude in the breathing frequency distribution. Both embodiments are envisioned.

By way of illustration, FIG. 2C illustrates a heartbeat spectrum 28. The X-axis indicates a frequency "f". The Y-axis indicates a coefficient related to energy amplitude of heartbeat spectrum 28, such that a higher coefficient corresponds to an energy amplitude of greater magnitude. As depicted in FIG. 2C, frequency $f_2$ may correspond to the highest coefficient of energy amplitude of heartbeat spectrum 28, referred to and labeled as $c_2$. Frequency $f_1$ may correspond to the particular frequency determined and/or derived from a breathing frequency distribution. Frequency $f_1$ may correspond to a coefficient of energy amplitude of heartbeat spectrum 28, referred to and labeled as $c_1$. Heart rate coherence may be based on the coefficient of energy amplitude of heartbeat spectrum 28, as depicted in FIG. 2C. In some embodiments, heart rate coherence may be defined as $c_1$. In some embodiments, heart rate coherence may be defined as $c_2$. In some embodiments, heart rate coherence may be defined based on $c_1$ and $c_2$.

Referring to FIG. 1, the target breathing rate and the target breathing phases that corresponds to the highest value of heart rate coherence may not correspond to the highest value of heart rate variability for individual subjects. Operation of system 100 may aim to increase and/or optimize either heart rate variability, heart rate coherence, and/or a combination of both.

In some embodiments, therapy module 113 may run and/or control a titrating algorithm to adjust levels of gas parameters throughout a therapy session. Titration and/or other adjustments may be performed in accordance with a therapy regimen and/or operating guidelines. For example, inspiratory pressure support may be adjusted within a range of pressures, having a minimum level and a maximum level of inspiratory pressure.

In some embodiments, information from system 100 and/or any of its constituent components may be stored and/or transferred to enable analysis and/or inspection, for example by one or more of user 108, a respiratory trainer, and/or a software application configured to determine performance and/or trends over time. For example, one or more parameters pertaining to a particular user may be stored and/or tracked over one week, one month, six months, one year, and/or other appropriate periods of time to determine performance and/or trends over this period. For example, information pertaining to heart rate variability and/or heart rate coherence may be tracked over this period to determine whether the (respiratory) therapy of subject 106 may have caused (and/or correlated to) improvements in any of the tracked parameters.

FIG. 3 illustrates a method 300 for improving heart rate coherence and/or heart rate variability of a subject. The operations of method 300 presented below are intended to be illustrative. In certain embodiments, method 300 may be accomplished with one or more additional operations not described, and/or without one or more of the operations discussed. Additionally, the order in which the operations of method 300 are illustrated in FIG. 3 and described below is not intended to be limiting.

In certain embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, a pressurized flow is generated for delivery to the airway of the subject, the pressurized flow including breathable gas. In some embodiments, operation 302 is performed by a pressure generator the same as or similar to pressure generator 140 (shown in FIG. 1 and described herein).

At an operation 304, output signals are generated conveying information related to one or more gas parameters of the pressurized flow of breathable gas, and a heart rate of the subject. In some embodiments, operation 304 is performed by sensors the same as or similar to sensors 142 (shown in FIG. 1 and described herein).

At an operation 306, levels of one or more gas parameters of the pressurized flow of breathable gas are adjusted to provide breathing cues to the subject that prompt the subject to transition between breathing phases. In some embodiments, operation 306 is performed by a control module the same as or similar to control module 111 (shown in FIG. 1 and described herein).

At an operation 308, a breathing rate and breathing phases of the subject are determined based on the generated output signals. In some embodiments, operation 308 is performed by a respiratory parameter determination module the same as or similar to respiratory parameter determination module 112 (shown in FIG. 1 and described herein).

At an operation 310, a heart rate variability for the subject is determined. The heart rate variability is based on the heart rate of the subject. In some embodiments, operation 310 is performed by a coronary parameter determination module the same as or similar to coronary parameter determination module 113 (shown in FIG. 1 and described herein).

At an operation 312, a target breathing rate range and target breathing phases are determined for which the heart rate variability is phase-aligned with the breathing rate and breathing phases of the subject. Adjustments of the levels of one or more gas parameters of the pressurized flow of breathable gas guide the subject to breathe are made according to the determined target breathing phases and within the determined target breathing rate range. In some embodiments, operation 312 is performed by a target module and a control module the same as or similar to target module 114 and control module 111 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system for improving heart rate coherence of a subject, the system comprising:
   a pressure generator configured to generate a pressurized flow of breathable gas for delivery to the airway of the subject;
   sensors configured to generate output signals conveying information related to:
      i) one or more gas parameters of the pressurized flow of breathable gas, and
      ii) a heart rate of the subject,
   one or more processors configured to execute processing modules, the processing modules comprising:
      a control module configured to adjust levels of one or more gas parameters of the pressurized flow of breathable gas to provide breathing cues to the subject that prompt to transition between breathing phases;
      a respiratory parameter determination module configured to determine a breathing rate and breathing phases of the subject based on the generated output signals;
      a coronary parameter determination module configured to determine a heart rate variability for the subject, wherein the heart rate variability is based on the heart rate of the subject;
      a domain conversion module configured to convert (i) the breathing rate to a breathing frequency distribution and (ii) the heart rate to a heart frequency distribution; and
      a target module configured to determine a target breathing rate range and target breathing phases for which the heart rate variability is phase-aligned with the breathing rate and breathing phases of the subject,
   wherein the control module adjusts the levels of one or more gas parameters of the pressurized flow of breathable gas to guide the subject to breathe according to the determined target breathing phases and within the determined target breathing rate range, and wherein the coronary parameter determination module is further configured to determine a heart rate coherence of the subject based on the heart frequency distribution and the breathing frequency distribution.

2. The system of claim 1, wherein the target module is further configured to determine a target breathing rate within the target breathing rate range, wherein the target module is further configured to determine whether modifications of the target breathing rate within the target breathing rate range correspond to an increase of the heart rate variability.

3. The system of claim 2, wherein adjustments by the control module guide the subject to breathe such that the heart rate variability of the subject is increased.

4. The system of claim 1, wherein the sensors are further configured to generate one or more output signals conveying information related to one or more physiological parameters that include one or more of a blood pressure, an oxygen saturation parameter, a level of brain activity, and/or a heart function, wherein the target module is further configured to determine one or more target levels for the one or more physiological parameters, and wherein the control module adjusts the levels of one or more gas parameters of the pressurized flow of breathable gas to guide the subject to breathe in such a way that the one or more physiological parameters are affected to more closely match the one or more target levels.

5. A method for improving heart rate coherence, the method being implemented in a system including a pressure generator and sensors, the method comprising;
generating output signals conveying information related to:
one or more gas parameters of a pressurized flow of breathable gas being delivered to the airway of a subject; and
a heart rate of the subject;
determining adjustments of levels of one or more gas parameters of the pressurized flow of breathable gas, wherein the adjustments provide breathing cues to the subject that prompt the subject to transition between breathing phases;
determining a breathing rate and breathing phases of the subject based on the generated output signals;
determining a heart rate variability for the subject, wherein the heart rate variability is based on the heart rate of the subject;
determining a target breathing rate range and target breathing phases for which the heart rate variability is phase-aligned with the breathing rate and breathing phases of the subject, wherein the adjustments of the levels of one or more gas parameters of the pressurized flow of breathable gas are in accordance with the determined target breathing phases and the determined target breathing rate range;
converting the breathing rate to a breathing frequency distribution;
converting the heart rate to a heart frequency distribution; and
determining a heart rate coherence of the subject based on the heart frequency distribution and the breathing frequency distribution.

6. The method of claim 5, further comprising:
determining whether modifications of a target breathing rate within the target breathing rate range correspond to an increase of the heart rate variability; and
responsive to the determination, determining adjustments of the levels of one or more gas parameters in accordance with an increase of the heart rate variability of the subject.

7. The method of claim 5, further comprising:
generating one or more output signals conveying information related to one or more physiological parameters that include one or more of a blood pressure, an oxygen saturation parameter, a level of brain activity, and/or a heart function;
determining one or more target levels for the one or more physiological parameters,
wherein the adjustments of the levels of one or more gas parameters of the pressurized flow of breathable gas are in accordance with effectuating one or more changes in the one or more physiological parameters to more closely match the one or more target levels.

8. The method of claim 5, wherein the heart rate variability is phase-aligned with breathing phases responsive to a determination that peaks in the heart rate and peaks of inspiratory flow rate are less than a predetermined period of time apart.

9. A system for improving heart rate coherence, the system comprising:
means for generating a pressurized flow of breathable gas for delivery to the airway of the subject;
means for generating output signals conveying information related to:
one or more gas parameters of the pressurized flow of breathable gas, and
a heart rate of the subject;
means for adjusting levels of one or more gas parameters of the pressurized flow of breathable gas to provide breathing cues to the subject that prompt the subject to transition between breathing phases;
means for determining a breathing rate and breathing phases of the subject based on the generated output signals;
means for determining a heart rate variability for the subject, wherein the heart rate variability is based on the heart rate of the subject;
means for determining a target breathing rate range and target breathing phases for which the heart rate variability is phase-aligned with the breathing rate and breathing phases of the subject, wherein the means for adjusting levels of one or more gas parameters guides the subject to breathe according to the determined target breathing phases and within the determined target breathing rate range;
means for converting the breathing rate to a breathing frequency distribution;
means for converting the heart rate to a heart frequency distribution; and
means for determining a heart rate coherence of the subject based on the heart frequency distribution and the breathing frequency distribution.

10. The system of claim 9, further comprising;
means for determining whether modifications of a target breathing rate within the target breathing rate range correspond to an increase of the heart rate variability,
wherein the means for adjusting levels of one or more gas parameters guides the subject to breathe such that the heart rate variability of the subject is increased.

11. The system of claim 9, further comprising:
means for generating one or more output signals conveying information related to one or more physiological parameters that include one or more of a blood pressure, an oxygen saturation parameter, a level of brain activity, and/or a heart function;

means for determining one or more target levels for the one or more physiological parameters, wherein the means for adjusting levels of one or more gas parameters guides the subject to breathe in such a way that the one or more physiological parameters are affected to more closely match the one or more target levels.

12. The system of claim 9, wherein the heart rate variability is phase-aligned with breathing phases responsive to a determination that peaks in the heart rate and peaks of inspiratory flow rate are less than a predetermined period of time apart.

13. A system for improving heart rate coherence of a subject, the system comprising:

a pressure generator configured to generate a pressurized flow of breathable gas for delivery to the airway of the subject;

sensors configured to generate output signals conveying information related to:
  i) one or more gas parameters of the pressurized flow of breathable gas, and
  ii) a heart rate of the subject, one or more processors configured to execute processing modules, the processing modules comprising:
  a control module configured to adjust levels of one or more gas parameters of the pressurized flow of breathable gas to provide breathing cues to the subject that prompt to transition between breathing phases;
  a respiratory parameter determination module configured to determine a breathing rate and breathing phases of the subject based on the generated output signals;
  a coronary parameter determination module configured to determine a heart rate variability for the subject, wherein the heart rate variability is based on the heart rate of the subject;
  a target module configured to determine a target breathing rate range and target breathing phases for which the heart rate variability is phase-aligned with the breathing rate and breathing phases of the subject; and
  a domain conversion module configured to convert (i) the breathing rate to a breathing frequency distribution and (ii) the heart rate to a heart frequency distribution, wherein the control module adjusts the levels of one or more gas parameters of the pressurized flow of breathable gas to guide the subject to breathe according to the determined target breathing phases and within the determined target breathing rate range, wherein the respiratory parameter determination module is further configured to determine a fundamental frequency of the breathing frequency distribution, wherein the coronary parameter determination module is further configured to determine a heart rate coherence of the subject, wherein the heart rate coherence is based on a magnitude of a coefficient related to energy amplitude of the heart frequency distribution at the fundamental frequency of the breathing frequency distribution, and wherein adjustments by the control module guide the subject to breathe such that the heart rate coherence of the subject is increased.

14. A method for improving heart rate coherence, the method being implemented in a system including a pressure generator and sensors, the method comprising;

generating output signals conveying information related to:
  one or more gas parameters of a pressurized flow of breathable gas being delivered to the airway of a subject; and
  a heart rate of the subject;

determining adjustments of levels of one or more gas parameters of the pressurized flow of breathable gas, wherein the adjustments provide breathing cues to the subject that prompt the subject to transition between breathing phases;

determining a breathing rate and breathing phases of the subject based on the generated output signals;

determining a heart rate variability for the subject, wherein the heart rate variability is based on the heart rate of the subject;

determining a target breathing rate range and target breathing phases for which the heart rate variability is phase-aligned with the breathing rate and breathing phases of the subject, wherein the adjustments of the levels of one or more gas parameters of the pressurized flow of breathable gas are in accordance with the determined target breathing phases and the determined target breathing rate range;

converting the breathing rate to a breathing frequency distribution;

converting the heart rate to a heart frequency distribution;

determining a fundamental frequency of the breathing frequency distribution; and determining a heart rate coherence of the subject, wherein the heart rate coherence is based on a magnitude of a coefficient related to energy amplitude of the heart frequency distribution at the fundamental frequency of the breathing frequency distribution, wherein the adjustments of the levels of one or more gas parameters of the pressurized flow of breathable gas guide the subject to breathe such that the heart rate coherence of the subject is increased.

15. A system for improving heart rate coherence, the system comprising:

means for generating a pressurized flow of breathable gas for delivery to the airway of the subject;

means for generating output signals conveying information related to:
  one or more gas parameters of the pressurized flow of breathable gas, and
  a heart rate of the subject;

means for adjusting levels of one or more gas parameters of the pressurized flow of breathable gas to provide breathing cues to the subject that prompt the subject to transition between breathing phases;

means for determining a breathing rate and breathing phases of the subject based on the generated output signals;

means for determining a heart rate variability for the subject, wherein the heart rate variability is based on the heart rate of the subject;

means for determining a target breathing rate range and target breathing phases for which the heart rate variability is phase-aligned with the breathing rate and breathing phases of the subject, wherein the means for adjusting levels of one or more gas parameters guides the subject to breathe according to the determined target breathing phases and within the determined target breathing rate means for converting the breathing rate to a breathing frequency distribution;

means for converting the heart rate to a heart frequency distribution;

means for determining a fundamental frequency of the breathing frequency distribution;

means for determining a heart rate coherence of the subject, wherein the heart rate coherence is based on a magnitude of a coefficient related to energy amplitude of the heart frequency distribution at the fundamental frequency of the breathing frequency distribution; and means for determining whether modifications of a target breathing rate within the target breathing rate range correspond to an increase of the heart rate coherence, wherein the means for adjusting levels of one or more gas parameters guides the subject to breathe such that the heart rate coherence of the subject is increased.

\* \* \* \* \*